US007577573B2

(12) United States Patent  
Janas, III et al.

(10) Patent No.: US 7,577,573 B2  
(45) Date of Patent: Aug. 18, 2009

(54) MEDICAL SUPPORT SYSTEM

(75) Inventors: John J. Janas, III, Concord, NH (US); John Robert Thompson, Little Rock, AR (US); Michael Robert Lustig, Newport News, VA (US)

(73) Assignee: General Electric Company, Schenectady, NY (US)

( * ) Notice: Subject to any disclaimer, the term of this patent is extended or adjusted under 35 U.S.C. 154(b) by 807 days.

(21) Appl. No.: 10/017,652

(22) Filed: Dec. 12, 2001

(65) Prior Publication Data

US 2003/0110059 A1     Jun. 12, 2003

(51) Int. Cl.  
  G06Q 10/00   (2006.01)  
  G06Q 50/00   (2006.01)
(52) U.S. Cl. ......................................................... 705/2
(58) Field of Classification Search .................. 705/2–3  
See application file for complete search history.

(56) References Cited

U.S. PATENT DOCUMENTS

| | | | | |
|---|---|---|---|---|
| 5,809,476 | A * | 9/1998 | Ryan .............................. | 705/2 |
| 6,047,259 | A * | 4/2000 | Campbell et al. ............... | 705/3 |
| 6,081,786 | A * | 6/2000 | Barry et al. .................... | 705/3 |
| 6,113,540 | A * | 9/2000 | Iliff ............................ | 600/300 |
| 6,283,761 | B1 * | 9/2001 | Joao ........................... | 434/236 |
| 6,748,353 | B1 * | 6/2004 | Iliff ............................... | 704/9 |
| 2002/0022975 | A1 * | 2/2002 | Blasingame et al. ........... | 705/3 |

OTHER PUBLICATIONS

Robert, Josephine J. "MEDRIS: Design software engineering of a hypermedia medical record input system" 1991. Illinois Institute of Technology.*  
Oliver, Neal Conrad, Ph.D. "A sublanguage based medical language processing system for German" 1992. New York University.*

* cited by examiner

*Primary Examiner*—Gerald J. O'Connor  
*Assistant Examiner*—Sheetal R Rangrej  
(74) *Attorney, Agent, or Firm*—Hanley, Flight & Zimmerman, LLC

(57) ABSTRACT

A medical support system and method for performing at least one medical support process relating to diagnosis and treatment of a medical condition and that includes or employs medical records relating to patients and medical support databases including medical guidelines for the diagnosis and treatment of a medical condition. A medical support process includes one or more process phases, which may include a data phase, a diagnostic phase and a therapy/treatment recommendation phase. Each process phase includes one or more process operations wherein each of the process operations of a process phase includes one or more process forms providing interfaces between a user and the process operations. Each process form includes fields for passing user inputs to the process operations and for displaying the results of the process operations to the user and the support processes are responsive to user inputs, the medical records and the guidelines to execute an interactive dialogue between the medical support process and the user to provide guidance to the user in performing the medical support process according to the guidelines and dependent upon the user inputs and the medical record.

20 Claims, 17 Drawing Sheets

FIG. 4A

| LIPID O&E.CCC  LISA LIPID | | |
|---|---|---|
| LIPID O&E | INFORMATION | |

COPYRIGHT 2001 CLINICAL CONTENT CONSULTANTS, LLC

LIPID MANAGEMENT    ENTER DIAGNOSIS OF HYPERLIPIDEMIA IN PROBLEM LIST IF APPROPRIATE.    [ADD PROBLEM]

| MOST RECENT LABS | LIPID FLOWSHEET | VIEW CURRENT LIPID MEDS | THERAPEUTIC RECOMMENDATIONS |

NCEP ADULT TREATMENT PANEL III RISK FACTORS    LIPID GOAL CALCULATOR BASED ON # RISK FACTORS

| | | | CLICK ACTION BUTTON FOR NCEP RECOMMENDED LIPID GOALS. TO CHANGE THE RECOMMENDED VALUES, ENTER DIFFERENT VALUES DIRECTLY IN THE FIELDS BELOW. |
|---|---|---|---|
| AGE 55 OR GREATER | ○ YES | ● NO | |
| EARLY MENOPAUSE W/O HRT | ○ YES | ○ NO | |
| DIABETES | ● YES | ○ NO | |
| HDL < 40 MG/DL | ○ YES | ● NO | |
| HDL > 60 MG/DL (NEG RISK FACTOR) | ○ YES | ● NO | |

0-1 RISK FACTORS

| | CHOL: | LDL: | ADL: | TRIG: |
|---|---|---|---|---|
| GOALS: | 200 | 160 | 40 | 200 |
| LAST VALUE: | 250 | 172 | 44 | 198 |
| LAST DATE: | 02/07/2001 | 02/07/2001 | 02/07/2001 | 02/07/2001 |
| NEXT DUE: | 02/07/2002 | 02/07/2002 | 02/07/2002 | 02/07/2002 |

| FH OF CARDIOVASCULAR DISEASE: | | | |
|---|---|---|---|
| MI IN FEMALE AGE < 55 | ● YES | ○ NO | |
| MI IN MALE AGE < 55 | ○ YES | ○ NO | |
| SMOKING STATUS | ○ QUIT | ○ CURRENT | ○ NEVER |

[?]  ALL LIPID GOALS HAVE NOT BEEN MET.

| HYPERTENSION | ● YES | ○ NO |
|---|---|---|
| ASHD-LVH, ANGINA, MI, CABG | ○ YES | ○ NO |
| STROKE OR TIA | ○ YES | ○ NO |
| PERIPHERAL VASCULAR DISEASE | ● YES | ○ NO |
| ABDOMINAL AORTIC ANEURYSM | ○ YES | ○ NO |

CONSIDER INTERVENTIONS TO LOWER LDL. HDL GOAL HAS BEEN MET. TRIGLYCERIDE GOAL HAS BEEN MET.

LIPID GOALS MET?    ○ YES    ○ NO
PLEASE DOCUMENT LIPID GOAL COMPLIANCE ABOVE.

| PREV FORM (CTRL+PGUP) | NEXT FORM (CTRL+PGDN) | | CLOSE |

FIG. 4B

LIPID O&E.CCC   LISA LIPID
COPYRIGHT 2001 CLINICAL CONTENT CONSULTANTS, LLC

| LIPID O&E | INFORMATION |

LIPID MANAGEMENT

| MOST RECENT LABS | LIPID FLOWSHEET | VIEW CURRENT LIPID MEDS | THERAPEUTIC RECOMMENDATIONS |

NCEP ADULT TREATMENT PANEL III RISK FACTORS

LIPID GOAL CALCULATOR BASED ON # RISK FACTORS
CLICK ACTION BUTTON FOR NCEP RECOMMENDED LIPID GOALS. TO
CHANGE THE RECOMMENDED VALUES, ENTER DIFFERENT VALUES
DIRECTLY IN THE FIELDS BELOW.

- AGE 55 OR GREATER — ○ YES  ⊙ NO
- EARLY MENOPAUSE W/O HRT — ○ YES  ○ NO
- DIABETES — ⊙ YES  ○ NO
- HDL < 40 MG/DL — ○ YES  ⊙ NO
- HDL > 60 MG/DL (NEG RISK FACTOR) — ⊙ YES  ○ NO
- FH OF CARDIOVASCULAR DISEASE:
  - MI IN FEMALE AGE < 55 — ⊙ YES  ○ NO
  - MI IN MALE AGE < 55 — ○ YES  ○ NO
- SMOKING STATUS — ○ QUIT  ○ CURRENT  ○ NEVER
- HYPERTENSION — ⊙ YES  ○ NO
- ASHD-LVH, ANGINA, MI, CABG — ○ YES  ○ NO
- STROKE OR TIA — ○ YES  ○ NO
- PERIPHERAL VASCULAR DISEASE — ○ YES  ○ NO
- ABDOMINAL AORTIC ANEURYSM — ○ YES  ○ NO

GOALS:        CHOL: [200]   LDL: [100]  [DIABETES]  HDL: [40]   TRIG: [200]
LAST VALUE:   250           172                     44          198
LAST DATE:    02/07/2001    02/07/2001              02/07/2001  02/07/2001
NEXT DUE:     6-8 WEEKS     6-8 WEEKS               6-8 WEEKS   6-8 WEEKS
              [?]           ALL LIPID GOALS HAVE NOT BEEN MET.  [?]
CONSIDER INTERVENTIONS TO LOWER LDL. HDL GOAL HAS BEEN MET.
TRIGLYCERIDE GOAL HAS BEEN MET.

LIPID GOALS MET ?   ○ YES   ○ NO
PLEASE DOCUMENT LIPID GOAL COMPLIANCE ABOVE.

[CLOSE]

[PREV FORM (CTRL+PGUP)]   [NEXT FORM (CTRL+PGDN)]

FIG.4C

LIPID O&E.CCC LISA LIPID

| LIPID O&E | INFORMATION | COPYRIGHT 2001 CLINICAL CONTENT CONSULTANTS, LLC |

LIPID MANAGEMENT

| MOST RECENT LABS | LIPID FLOWSHEET | VIEW CURRENT LIPID MEDS | THERAPEUTIC RECOMMENDATIONS |

NCEP ADULT TREATMENT PANEL III RISK FACTORS

| | | | LIPID GOAL CALCULATOR BASED ON # RISK FACTORS |
|---|---|---|---|
| AGE 55 OR GREATER | ○ YES | ⦿ NO | CLICK ACTION BUTTON FOR NCEP RECOMMENDED LIPID GOALS. TO |
| EARLY MENOPAUSE W/O HRT | ○ YES | ○ NO | CHANGE THE RECOMMENDED VALUES, ENTER DIFFERENT VALUES |
| DIABETES | ⦿ YES | ○ NO | DIRECTLY IN THE FIELDS BELOW. |
| HDL < 40 MG/DI | ○ YES | ⦿ NO | |
| HDL > 60 MG/DI (NEG RISK FACTOR) | ○ YES | ⦿ NO | Hx OF CAD, PVD, CVA, TIA OR AORTIC ANEURYSM |
| FH OF CARDIOVASCULAR DISEASE: | | | CHOL: LDL: ADL: TRIG: |
| MI IN FEMALE AGE < 55 | ⦿ YES | ○ NO | GOALS: 200 100 40 200 |
| MI IN MALE AGE < 55 | ○ YES | ○ NO | LAST VALUE: 250 172 44 198 |
| SMOKING STATUS  ○ CURRENT | ○ QUIT | ○ NEVER | LAST DATA: 02/07/2001 02/07/2001 02/07/2001 02/07/2001 |
| HYPERTENSION | ⦿ YES | ○ NO | NEXT DUE: 6-8 WEEKS 6-8 WEEKS 6-8 WEEKS 6-8 WEEKS |
| ASHD-LVH, ANGINA, MI, CABG | ○ YES | ○ NO | [?] ALL LIPID GOALS HAVE NOT BEEN MET. |
| STROKE OR TIA | ○ YES | ○ NO | CONSIDER INTERVENTIONS TO LOWER LDL. HDL GOAL HAS BEEN MET. |
| PERIPHERAL VASCULAR DISEASE | ⦿ YES | ○ NO | TRIGLYCERIDE GOAL HAS BEEN MET. |
| ABDOMINAL AORTIC ANEURYSM | ○ YES | ○ NO | |
| | | | LIPID GOALS MET ?   ○ YES   ○ NO |
| | | | PLEASE DOCUMENT LIPID GOAL COMPLIANCE ABOVE. |

| PREV FORM (CTRL+PGUP) | NEXT FORM (CTRL+PGDN) | CLOSE |

FIG. 4D

LIPID O&E.CCC  USA LIPID

| LIPID O&E | INFORMATION | | COPYRIGHT 2001 CLINICAL CONTENT CONSULTANTS, LLC |

LIPID MANAGEMENT

| MOST RECENT LABS | LIPID FLOWSHEET | VIEW CURRENT LIPID MEDS | THERAPEUTIC RECOMMENDATIONS |

NCEP ADULT TREATMENT PANEL III RISK FACTORS         LIPID GOAL CALCULATOR BASED ON # RISK FACTORS

AGE 55 OR GREATER                   ○ YES  ⊙ NO     CLICK ACTION BUTTON FOR NCEP RECOMMENDED LIPID GOALS. TO
EARLY MENOPAUSE W/O HRT             ○ YES  ○ NO     CHANGE THE RECOMMENDED VALUES, ENTER DIFFERENT VALUES
DIABETES                            ○ YES  ○ NO                    DIRECTLY IN THE FIELDS BELOW.
HDL < 40  MG/DL                     ○ YES  ⊙ NO
HDL > 60  MG/DL (NEG RISK FACTOR)   ○ YES  ⊙ NO                        [ 0-1 RISK FACTORS ]
FH OF CARDIOVASCULAR DISEASE:
   MI IN FEMALE AGE < 55            ○ YES  ○ NO              CHOL:      LDL:      ADL:      TRIG:
   MI IN MALE AGE < 55              ○ YES  ○ NO     GOALS:   [200]     [160]     [40]     [200]
SMOKING STATUS   ○ CURRENT  ○ QUIT  ○ NEVER         LAST VALUE: 250       172       44        198
HYPERTENSION                        ○ YES  ○ NO     LAST DATA: 02/07/2001 02/07/2001 02/07/2001 02/07/2001
ASHD-LVH, ANGINA, MI, CABG          ○ YES  ○ NO     NEXT DUE:  02/07/2002 02/07/2002 02/07/2002 02/07/2002
STROKE OR TIA                       ○ YES  ○ NO       [?]  ALL LIPID GOALS HAVE NOT BEEN MET.              [?]
PERIPHERAL VASCULAR DISEASE         ○ YES  ○ NO     CONSIDER INTERVENTIONS TO LOWER LDL. HDL GOAL HAS BEEN MET.
ABDOMINAL AORTIC ANEURYSM           ○ YES  ○ NO              TRIGLYCERIDE GOAL HAS BEEN MET.

LIPID GOALS MET ?     ○ YES     ○ NO
                                                       PLEASE DOCUMENT LIPID GOAL COMPLIANCE ABOVE.

[ PREV FORM (CTRL+PGUP) ]  [ NEXT FORM (CTRL+PGDN) ]                                    [ CLOSE ]

FIG. 4E

LIPID O&E.CCC   LISA LIPID

| LIPID O&E | INFORMATION | COPYRIGHT 2001 CLINICAL CONTENT CONSULTANTS, LLC |

LIPID MANAGEMENT

| MOST RECENT LABS | LIPID FLOWSHEET | VIEW CURRENT LIPID MEDS | THERAPEUTIC RECOMMENDATIONS |

NCEP ADULT TREATMENT PANEL III RISK FACTORS    LIPID GOAL CALCULATOR BASED ON # RISK FACTORS

| | | | |
|---|---|---|---|
| AGE 55 OR GREATER | ○ YES | ● NO | |
| EARLY MENOPAUSE W/O HRT | ○ YES | ○ NO | |
| DIABETES | ○ YES | ○ NO | |
| HDL < 40 MG/DL | ○ YES | ● NO | |
| HDL > 60 MG/DL (NEG RISK FACTOR) | ○ YES | ● NO | |
| FH OF CARDIOVASCULAR DISEASE: | | | |
| MI IN FEMALE AGE < 55 | ● YES | ○ NO | |
| MI IN MALE AGE < 55 | ○ YES | ○ NO | |
| SMOKING STATUS    ○ CURRENT | ○ QUIT | ● NEVER | |
| HYPERTENSION | ● YES | ○ NO | |
| ASHD-LVH, ANGINA, MI, CABG | ○ YES | ○ NO | |
| STROKE OR TIA | ○ YES | ○ NO | |
| PERIPHERAL VASCULAR DISEASE | ○ YES | ○ NO | |
| ABDOMINAL AORTIC ANEURYSM | ○ YES | ○ NO | |

CLICK ACTION BUTTON FOR NCEP RECOMMENDED LIPID GOALS. TO
CHANGE THE RECOMMENDED VALUES, ENTER DIFFERENT VALUES
DIRECTLY IN THE FIELDS BELOW.

2 OR MORE RISK FACTORS <20% 10YT CHD

| | CHOL: | LDL: | HDL: | TRIG: |
|---|---|---|---|---|
| GOALS: | 200 | 130 | 40 | 200 |
| LAST VALUE: | 250 | 172 | 44 | 198 |
| LAST DATA: | 02/07/2001 | 02/07/2001 | 02/07/2001 | 02/07/2001 |
| NEXT DUE: | 3 MONTHS | 3 MONTHS | 3 MONTHS | 3 MONTHS |

[?]   ALL LIPID GOALS HAVE NOT BEEN MET.
CONSIDER INTERVENTIONS TO LOWER LDL. HDL GOAL HAS BEEN MET.
TRIGLYCERIDE GOAL HAS BEEN MET.

LIPID GOALS MET ?   ○ YES   ○ NO   [?]
PLEASE DOCUMENT LIPID GOAL COMPLIANCE ABOVE.

| PREV FORM (CTRL+PGUP) | NEXT FORM (CTRL+PGDN) | | CLOSE |

LIPID O&E.CCC   LISA LIPID

| LIPID O&E | INFORMATION |

COPYRIGHT 2001 CLINICAL CONTENT CONSULTANTS, LLC

THE PATIENT'S 10 YEAR CORONARY HEART DISEASE RISK IS CALCULATED TO BE: 6%

THE FOLLOWING 7 CATEGORIES ARE USED TO CALCULATE THIS RISK PROFILE:   [VIEW CATEGORIES]

NCEP III CRITERIA TO DETERMINE DESIRED LDL GOALS:   [VIEW CRITERIA]

LOGICIAN MESSAGE                                [X]
(?)   AGE                  7 POINTS
      HDL                  1 POINTS
      TOTAL CHOLESTEROL    3 POINTS
      SYSTOLIC BP          NO VALUE
      SMOKING STATUS       0 POINTS
      DIABETES             0 POINTS
      LVH                  0 POINTS

[YES]     [NO]

COPYRIGHT 2001; CLINICAL C...........ERVED); ID #:CCC.0024

[PREV FORM (CTRL+PGUP)]   [NEXT FORM (CTRL+PGDN)]                                    [CLOSE]

FIG.4F

FIG. 4I

LIPID O&E.CCC   LISA LIPID

LIPID O&E | INFORMATION | LOGICIAN MESSAGE

LIPID MANAGEME

MOST RECENT LAB

NCEP ADULT TREATM

| SECONDARY CAUSES FOR HYPERLIPIDEMIA INCLUDE: | | | |
|---|---|---|---|
|  | CHOLESTEROL | TRIGLYCERIDE | LOW HDL |
| DRUGS | | | |
| ANTIHYPERTENSIVES | | | |
| THIAZIDES | YES | YES | — |
| LOOP DURETIC | — | — | YES |
| B-BLOCKER | — | YES | YES |
| HORMONES | | | |
| GLUCOCORTICOIDS | YES | YES | — |
| ANDROGENS | YES | — | — |
| DCAs | — | YES | +/− |
| ESTROGENS | YES | YES | YES |
| PROGESTINS | — | — | YES |
| GROWTH HORMONE | — | YES | — |
| OTHERS | | | |
| AMIODARONS | YES | — | YES |
| FACUETINOIN | YES | YES | — |
| CYCLOSPORIN | YES | YES | — |
| CONDITIONS | | | |
| METABOLIC | | | |
| DIABETES | YES | YES | YES |
| HYPOTHYROIDISM | YES | YES | — |
| ANOREXIA NERVOSA | YES | — | — |
| OBESITY | — | YES | YES |
| PREGNANCY | YES | YES | — |
| ACROMEGLY | — | YES | — |
| HYPERGLYCEMIA | YES | — | — |

SEE SECOND PAGE (?2) FOR MORE...

YES   NO

AGE 55 OR GREATER
EARLY MENOPAUSE W/O
DIABETES
HDL < 40 MG/DI
HDL > 60 MG/DI (NEG R
FH OF CARDIOVASCULAR D
    MI IN FEMALE AG
    MI IN MALE AGE
SMOKING STATUS
HYPERTENSION
ASHD-LVH, ANGINA, M
STROKE OR TIA
PERIPHERAL VASCULAR DI
ABDOMINAL AORTIC ANEU
    PLEASE
    INSTR
    SECOND

?1  ?2

RECOMMENDATIONS

RISK FACTORS
ENDED LIPID GOALS. TO
NTER DIFFERENT VALUES
ELOW.
OF AORTIC ANEURYSM
ADL:   TRIG: 200
40     198
2/07/2001  02/07/2001
−8 WEEKS   6−8 WEEKS
EEN MET.   ?
DL GOAL HAS BEEN MET.
EN MET.        ● NO

PREV FORM (CTRL+PGUP)          CLOSE

LIPID O&E.CCC  LISA LIPID

| LIPID O&E | INFORMATION |

LIPID MANAGEM[LOGICIAN MESSAGE]                    COPYRIGHT 2001 CLINICAL CONTENT CONSULTANTS, LLC

MOST RECENT LAB                                                                                         RECOMMENDATIONS

NCEP ADULT TREATM          CRITERIA FOR DETERMINING WHEN REPEAT LIPID PROFILES ARE DUE:                 # RISK FACTORS

AGE 55 OR GREATER          IF PATIENT HAS CORONARY ARTERY DISEASE:                                      ENDED LIPID GOALS. TO
                                                                                                        TER DIFFERENT VALUES
EARLY MENOPAUSE W/O           1) IF NOT ON STATIN AND LDL > 100, THEN RECHECK LIPIDS IN 6-8 WEEKS.      ELOW.
DIABETES                      2) IF NOT ON STATIN AND LDL < 100, THEN RECHECK LIPIDS IN 3-6 MONTHS.
                              2) IF ON STATIN AND LDL > 100, THEN RECHECK LIPIDS IN 3 MONTHS.           OR AORTIC ANEURYSM
HDL < 40 MG/DL                4) IF ON STATIN AND LDL < 100, THEN RECHECK LIPIDS IN 3-6 MONTHS.         DL:         TRIG:
HDL > 60 MG/DL (NEG R                                                                                   0           200
FH OF CARDIOVASCULAR D     IF PATIENT HAS DIABETES:                                                     4           198
   MI IN FEMALE AG            1) IF NOT ON STATIN AND LDL > 100, THEN RECHECK LIPIDS IN 6-8 WEEKS.      2/07/2001  02/07/2001
   MI IN MALE AGE             2) IF NOT ON STATIN AND LDL < 100, THEN RECHECK LIPIDS IN 3-6 MONTHS.     -8 WEEKS   6-8 WEEKS
SMOKING STATUS                2) IF ON STATIN AND LDL > 100, THEN RECHECK LIPIDS IN 3 MONTHS.           EEN MET.        [?]
HYPERTENSION                  4) IF ON STATIN AND LDL < 100, THEN RECHECK LIPIDS IN 3-6 MONTHS.         DL GOAL HAS BEEN MET.
ASHD-LVH, ANGINA, M                                                                                     EN MET.
STROKE OR TIA              IF NEITHER CAD OR DIABETIC:
PERIPHERAL VASCULAR D         2 OR MORE RISK FACTORS AND LDL > 130, THEN RECHECK LIPIDS IN 3 MONTHS.       ○ NO
ABDOMINAL AORTIC ANE          1 RISK FACTOR AND LDL > 160, THEN RECHECK LIPIDS IN 3 MONTHS.             MPLIANCE ABOVE.
                              0 RISK FACTORS AND LDL > 190, THEN RECHECK LIPIDS IN 3 MONTHS.

DUE NOW IF NO LIPIDS HAVE EVER BEEN DONE OR THE LAST SET > 1 YEAR AGO,
                           OTHERWISE IF ON STATIN, RECHECK LIPIDS IN 3-6 MONTHS,
                           OTHERWISE IF NOT ON STATIN, RECHECK LIPIDS IN 1 YEAR.

*** NOTE: ALL LIPID DUE DATES WILL BE THE SAME DATE AND ARE SYNCHRONIZED WITH
                                     THE LDL DUE DATE ***

[ YES ]     [ NO ]

| PREV FORM (CTRL+PGUP) | NEXT FORM (CTRL+PGDN) |                                                       [ CLOSE ]

FIG. 4M

LIPID O&E.CCC USA LIPID

| LIPID O&E | INFORMATION |

COPYRIGHT 2001 CLINICAL CONTENT CONSULTANTS, LLC

LIPID MANAGEMENT

| MOST RECENT LABS | LIPID FLOWSHEET | VIEW CURRENT LIPID MEDS | THERAPEUTIC RECOMMENDATIONS |

NCEP ADULT TREATMENT PANEL III RISK FACTORS — LIPID GOAL CALCULATOR BASED ON # RISK FACTORS
CLICK ACTION BUTTON FOR NCEP RECOMMENDED LIPID GOALS. TO CHANGE THE RECOMMENDED VALUES, ENTER DIFFERENT VALUES DIRECTLY IN THE FIELDS BELOW.

- AGE 55 OR GREATER ● YES ○ NO
- EARLY MENOPAUSE W/O HRT ○ YES ○ NO
- DIABETES ○ YES ○ NO
- HDL < 40 MG/DI ○ YES ● NO
- HDL >
- FH OF  Hx OF CAD, PVD, CVA, TIA OR AORTIC ANEURYSM

LOGICIAN MESSAGE (?) NOTE: LAST SGOT > 50 (BUT LESS THAN 3 TIMES THE UPPER LIMIT OF NORMAL) AND IS ON AN HMG CoA REDUCLASE INHIBITOR (STATIN MONITOR LFT's CLOSELY EVERY 4-6 WEEKS UNTIL RETURN TO NORMAL CONSIDER HOLDING THE STATIN IF LFT's REMAIN) ELEVATED OR ARE CLIMBING.

CHOL: [ ]   LDL: [ ]   ADL: [ ]   TRIG: [X]

[ YES ]    [ NO ]    7/2001  WEEKS [?] EN MET.

- SMOKIN
- HYPERT
- ASHD—
- STROKE OR TIA ○ YES ○ NO
- PERIPHERAL VASCULAR DISEASE ○ YES ○ NO
- ABDOMINAL AORTIC ANEURYSM ○ YES ○ NO

- INSTRUCTION BY DIETICIAN OR TRAINED PERSONNEL? ● YES ○ NO
- SECONDARY CAUSES OF HYPERLIPIDEMIA RULED OUT? ● YES ○ NO
- COUNSELED ON ADJUNCTIVE MEASURES? ● YES ○ NO

LIPID GOALS MET ?  ○ YES  ● NO

ADJUNCTIVE MEASURES INCLUDE AEROBIC EXERCISE WEIGHT MANAGEMEN, ASA, VITAMIN E, MVI W/FOLIC ACID, EVALUATE ETOH CONSUMPTION STOSTANOL ESTES NUTRITION SUPPLEMENT

[?1] [?2]

[ PREV FORM (CTRL+PGUP) ]   [ NEXT FORM (CTRL+PGDN) ]   [ CLOSE ]

MEDICAL SUPPORT SYSTEM

FIELD OF THE INVENTION

The present invention is related to a method and system for service provider support in providing services involving complex interplay of factors, recommendations and guidelines and requirements from a range of sources, including judgment decisions, and in particular for information, decisions and reporting support in the providing of medical services.

BACKGROUND OF THE INVENTION

Many professions require that practitioners and para-practitioners make judgments and decisions based upon or influenced by a complex interplay of information, factors and requirements from a range of sources and as the result of executing complex procedures which in themselves may involve complex and even conflicting requirements. A typical example is the medical profession, wherein a doctor or paramedical, such as a nurse practitioner, is required to acquire and consider a large volume of present and historical patient information and to decide, based on that information, whether to acquire further information and what procedures or methods to use in acquiring the additional information. The practitioner is then required to evaluate the patients present and probable future conditions and trends or developments, and to decide whether changes in treatment are necessary and what those changes should be. These processes are further complicated in that the practitioner is presented with a continuous flow or even flood of new and continuously changing information, recommendations and requirements.

For example, there are one or more professional associations or groups associated with virtually every significant medical condition or disease. Each of these groups or organizations is engaged in the study of the disease of interest and in the generation of recommendations and guidelines for the treatment of the disease, which change frequently as more is learned about the disease. The medical treatment industry, including pharmaceutical companies, medical equipment companies, hospitals and other medical treatment related enterprises are in turn engaged in the continuous development of new medications and methods for treatment of diseases or medical conditions, and recommendations for the use of the new medications or methods. Yet other organizations, such as the medical insurance organizations of various types, issue medical treatment guidelines based upon the guidelines developed by the professional organizations and medical industry and upon their own requirements and goals. These goals and requirements not only change continuously, but may conflict with the guidelines and recommendations of, for example, the professional organizations or those of other insurance organizations.

As a result, the practitioner is faced with increasingly complex decision making processes, involving increasing volumes and types of information and sources of information, increasing and continuously changing guidelines and requirements, increasing numbers of medications and methods for treatment, and increasingly numerous and more complex decision points in the processes for providing care to a patient. These problems are further compounded in that the guidelines or requirements of the various organizations often disagree or are in conflict. For example, a professional organization may recommend one medication for treatment of a condition, one insurance company may require a second medication, and another insurance company may approve only a third medication. These guidelines and requirements, however, are typically based upon generalized, statistical information gathered from studies and represent "average" patients and conditions. The guidelines also tend to be influenced by the specific interests of each group, such as health insurance or management organizations with a strong interest in cost containment. The doctor, however, is most familiar with the specific patient and the current condition and history of the patient, and may recognize that a different medication or course of treatment is preferable. The problem is still further compounded in that many of the groups and organizations supporting the practitioner, such as professional organizations, the pharmaceutical companies and the insurance companies, also request or require increasing volumes of reports from the practitioners, further increasing the workloads on the practitioners.

As a consequence, practitioners are often overwhelmed with a flood of information regarding each specific patient, the current and changing tests, guidelines, recommendations, medications and treatments for various diseases or conditions, conflict among the requirements or recommendations of various professional or service organizations, and the various reporting requirements or requests. As a result, and despite experience, thorough professional training and all due care on the part of the practitioner, it is possible for a practitioner to miss or forget a factor, a test, a possible medication or a requirement or a guideline simply because of the number of factors to consider for a given patient and the current range and complexity of possible medical procedures, even within a specific disease or condition. A practitioner may, for example, overlook or be unaware of indications of a developing condition, a precautionary or recommended test, a possible medication or medication conflict, a changed guideline, or avoidable conflicts with recommendations, guidelines or reporting requirements. For example, a newly changed guideline may warn that a change in or value of a blood test factor that was previously held to be insignificant is now regarded as a warning or indicator of a condition for which a precautionary test is recommended. In a further example, certain insurance companies may approve payment for specific medications but not for equivalent medications, thereby leading to possible conflicts with insurance company requirements that could be avoided.

Various practitioner support systems of the prior art, such as record generation/retrieval systems, information retrieval systems and "expert" systems, have attempted to address these problems. Such systems of the prior art have generally been of only limited success, however, because they either do not address or only partially address the actual needs and methods of practice of the practitioners.

For example, electronic medical record (EMR) systems are in common use to generate and retrieve on-line medical records for individual patients. Such EMR systems, however, do not assist the practitioner in performing medical examination and treatment processes, often referred to as "patient encounters", but typically assist only by providing fast storage and retrieval of historical information pertaining to a patient. Because of the range and variety of medical information that could possibly be stored for a given patient, however, it is very difficult to create and maintain an electronic medical record having all of the necessary data storage fields for each patient and it is very difficult and time consuming to enter the medical data, such as test results and medications prescribed. As a result, EMR systems are often not used to their full potential. For example, many users attempt to implement paper record work flows in an EMR system, but fail to capture the true power of the EMR system, such as the digital storage of data which can be imported, exported, extracted and integrated to improve work flow and quality of care.

In a like manner, there are many on-line information retrieval systems available to the practitioner and through which a practitioner may search for and retrieve information pertaining to diagnostic symptoms, guidelines for treatment, medications and medication effects, insurance policies and requirements, and so on. While such information retrieval systems provide wide access to a vastly increased range of information, such systems are essentially merely substitutes for traditional hard copy references, such as the Merck manual. Again, such systems are too slow and cumbersome to be of assistance to the practitioner in real time patient encounters and many, if not most practitioners, tend to rely upon their experience and memory for such information during patient encounters or to refer to a hard copy of a reference work.

Lastly, there have been many attempts to create "expert" or "artificial intelligence" systems to aid medical practitioners, but such systems have been typically unsuccessful in practice for a number of fundamental reasons.

For example, "expert" systems which attempt to distill and provide the expertise of one or more experts in a given field are difficult to create because it is difficult, if not impossible, to insure that all of the required expert knowledge has in fact been extracted and embodied in the system. That is, and for example, a single expert may not have all of the desired knowledge, particularly in a large and complex field, and experts often disagree on essential matters, such as conditions for diagnosis and optimum treatment plans. In addition, human thought processes are extremely complex and are not well understood and experts often do not consciously understand how their minds reach a conclusion or retrieve a necessary bit of information. For example, a specific pattern of information may trigger an unconscious thought process and the retrieval of a critical bit of knowledge. The expert may be unaware of knowing that critical bit of knowledge on a conscious level, and the remembering may occur only for a very specific pattern of stimulus, so that it is virtually impossible to deliberately retrieve that information for inclusion in an expert system. For the same reasons, it is very difficult to maintain, update or correct such expert systems as knowledge and practices evolve.

While expert systems attempt to assist the practitioner by extending the practitioner's knowledge and, for example, analytical skills, "artificial intelligence" (AI) systems attempt to emulate the thought processes of the practitioner and to effectively either replace the practitioner or place a second practitioner at the human practitioner's shoulder. Artificial intelligence systems, however, not only have all of the problems of expert systems with regard to extracting and embodying knowledge, but also have unique problems that limit their use in many fields. For example, many AI systems are designed for and capable of "learning" or self-modification over time and with "experience". While this is one of the advantages and desired features of AI systems, it can be a problem in many applications due to uncertainty over time with respect to the rules, principles and information through which and upon which a system is currently providing advice or decisions. For these reasons, AI systems are often regarded as too uncertain or unreliable for certain applications, such as medical support services. There are also psychological problems with AI systems as practitioners are uncomfortable with systems that apparently attempt to replace the practitioners, or to at least displace or "second guess" their primary function, and patients are often uncomfortable dealing solely or primarily with a computer system rather than a human in medical matters.

The present invention provides a solution to these and other related problems of the prior art.

SUMMARY OF THE INVENTION

The present invention is directed to a medical support system and method for providing medical support for performing at least one medical support process relating to diagnosis and treatment of a medical condition.

According to the present invention, the system and method of the present invention includes or employs at least one medical record relating to a patient and at least one medical support database including medical guidelines for the diagnosis and treatment of the medical condition and performs a medical support process including at least one process phase. In the present invention, each process phase includes one or more process operations wherein each of the process operations of a process phase includes at least one process form. Each process form provides an interface between a user and the process operations of the process phase and each process form includes fields for passing user inputs to the process operations and for displaying the results of the process operations to the user wherein at least one support process is responsive to user inputs, the medical record and the guidelines for performing the process operations. The support processes thereby execute an interactive dialogue between the medical support process and the user to provide guidance to the user in performing the medical support process according to the guidelines and dependent upon the user inputs and the medical record.

According to the present invention, a medical support process typically includes a data phase for entering new information and reviewing historical information pertaining to the medical condition of the patient for the purposes of the medical support process, and an assessment phase for evaluation of the patient's present medical condition based upon the information from the data phase and the guidelines for the diagnosis and treatment of the medical condition. A medical support process may further include a recommendations phase including process operations and guidelines to assist the user in determining a course of treatment for the patient.

The process form fields include fields for the display and entry of data, text, prompts, messages and user decision options and may include process fields containing process calls invoking corresponding support processes upon corresponding user inputs to the process fields.

The support operations may include first support processes for invoking second support processes dependent upon user inputs, support processes for displaying a next process form, and support processes for modifying the information displayed in a present process form.

In further implementations of the present invention, the medical support databases may reside within the support processes, and a medical support system may include a dialect translator for translating between medical terms displayed to and entered by a user and corresponding equivalent, but different medical terms employed in the support operations.

The present invention addresses these and other problems of the prior art.

DESCRIPTION OF THE DRAWINGS

Other features, objects and advantages of the present invention will be understood by those of ordinary skill in the relevant arts after reading the following descriptions of a presently preferred embodiment of the present invention, and after examination of the drawings, wherein:

FIGS. 4A through 4M illustrate process forms and process form fields for an exemplary medical support process.

DETAILED DESCRIPTION OF THE INVENTION

Figure 1:
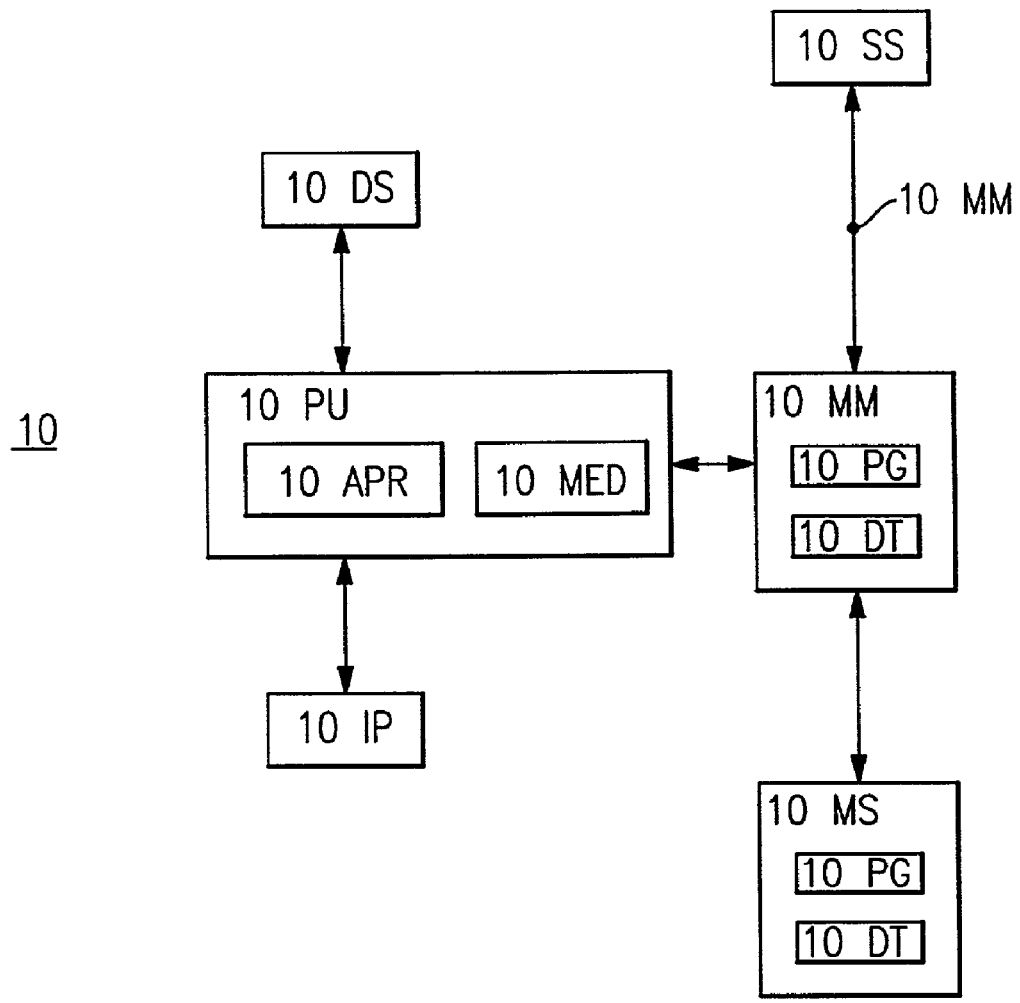
FIG. 1 is a block diagram of an exemplary system in which the present invention may be implemented.
Figure 2:
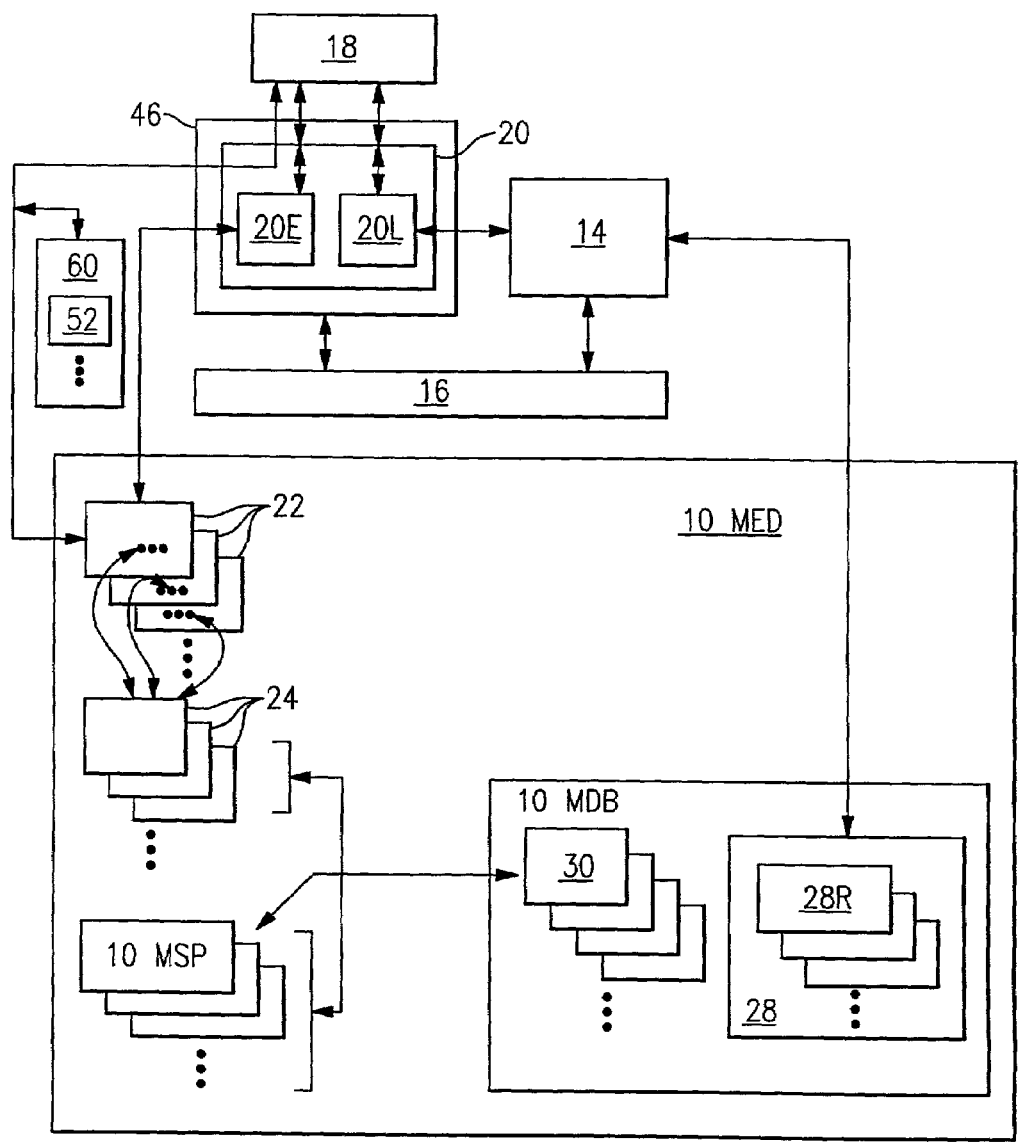
FIG. 2 is a block diagram illustrating a medical support system of the present invention.

Referring to FIGS. 1 and 2, therein is shown illustrative block diagrams of an exemplary Medical Support System (MSS) 10 implementing the present invention.

As indicated in FIG. 1, an MSS 10 will typically be implemented in a general purpose Computer System 10CS that will typically include a Processor Unit 10PU, a Memory 10MM with one or more associated Mass Storage Device 10MS for storing Programs 10PG and Data 10DT, one or more Input Devices 10ID for user inputs, such as a keyboard, mouse or touch screen, and a Display 10DS for display of information to a user. A MSS 10 may be implemented in, for example, a desktop, laptop or notebook computer, as terminals or computers networked with data and program Servers 10SS through local or wide area Networks 10NN, including wireless networks, or in wireless networked palmtop devices of appropriate memory, processing and display capacity.

As will be well understood by those of ordinary skill in the relevant arts, a MSS 10 will perform or execute Processes 10PR controlling, performing or supporting the functions and operations of the MSS 10, including, for example, the medical support system processes. The Processes 10PR of a MSS 10 will typically include, for example, Administrative Processes 10APR pertaining to the administrative and management functions of the MSS 10, such as operating system functions, and Medical Processes 10MED comprising the medical support system functions of the present invention. Processes 10PR are defined and controlled by Programs 10PG and, for example, user data input provided through Input Devices 10ID and data read from databases or other data sources, may reside in one or more Mass Storage Devices 10MS.

As will be described in the following, the Medical Processes 10MED comprising the medical support system functions of the present invention is not constrained to the generation and maintenance of patient medical records, although these operations are within the scope of functions supported by the Medical Processes 10MED. Instead, a MSS 10 of the present invention provides real time, interactive support for practitioners during patient encounters, such as prompts and reminders of necessary information or tests, advice and guidelines in diagnosis and treatment, decision support, therapeutic recommendations, educational information and the real time capture of metrics. The support provided by a MSS 10 of the present invention is based, for example, upon the best current recommendations of, for example, professional medical organizations, studies, health care/insurance guidelines, and so on. In this regard, however, a MSS 10 of the present invention does not attempt to supplant or replace the experience and judgment of the practitioner, but instead operates to maximize the workflow, mind flow and quality of practice by advisory support which may be overridden by the practitioner at any time based, for example, on the practitioner's experience or more specific knowledge regarding a particular patient.

According to the present invention, the system and method of the present invention includes or employs medical records relating to the patients and medical support databases including medical guidelines for the diagnosis and treatment of medical conditions according to current professional guidelines for the diagnosis and treatment of diseases and medical conditions and processes utilizing these databases to diagnose and recommend therapy or treatment for a patient in a manner that is supportive of but that does not interfere with the work and mind flow processes of the user. As will be described, a support process performed by a medical support system of the present invention executes an interactive dialogue between the medical support process and the user to provide guidance to the user in performing the medical support process according to the guidelines and dependent upon the user inputs and the medical record. A medical support process performed by the present invention for a given condition or disease includes one or more process phases, which may include a data entry and review phase, a diagnostic phase and a therapeutic/treatment recommendation phase, which are presented to a user through process forms providing graphic interfaces for the entry and display of information regarding the support process.

Referring to FIG. 2, it is illustrated therein that in a presently preferred and typical embodiment of a MSS 10, the Medical Processes 10MED of the present invention are constructed on and use the facilities and functions of a conventional Electronic Medical Record System (EMR) 12, such as MedicaLogic/Medscape Logician® from MedicaLogic/Medscape Corporation, and a conventional Database Program 14, such as an Oracle® server relational database. As is well understood in the relevant arts, in a conventional medical record system EMRs 12 and Database Programs 14 operate on an Operating Systems 16, such as Microsoft Windows®, and with either a thick or thin Client Interface 18, to construct, manage, store and retrieve patient medical records. It will be understood, however, that MedicaLogic/Medscape Logician® and the Oracle® database are representative and exemplary of a range of readily available, conventional electronic medical record programs and databases used to construct, manage, store and retrieve patient medical records. It will also be understood that these functions of a MSS 10 may be implemented through any similar or equivalent programs, or through corresponding programs generated specifically for a MSS 10.

As illustrated in FIG. 2, an EMR 12 typically includes an Interface Mechanism 20 which comprises a plurality of mechanisms and functions for entering data into and reading data from the associated databases. In MedicaLogic/Medscape Logician®, for example, this mechanism is referred to as the MedicaLogic Expression Language (MEL) and comprises a software code platform that allows input to and output from the relational database. An Interface Mechanism 20 will typically include a Language 20L which comprises defined terms and syntax for defining database records, the fields and contents of the database records, formulating queries and searches of the database records, relating and parsing the fields and contents of the database records, reading data from and entering data into the database records, and so on.

Interface Mechanism 20 will typically also include an Interface Form Editor 22 for the generation and construction of graphical user interfaces and displays of, for example, processes and database records supported and executed by the EMR 12 and associated databases. Such user interfaces and displays are typically structured and displayed as Forms 22 wherein a Form 22 comprises a structured array of Fields 24 for the display and entry of data, text, graphics, prompts, messages, "pop-up windows", and so on, to display to a user and to allow a user to interact with, for example, Medical Processes 10MED and the associated databases. For example, a user may enter data identifying a patient into certain Fields 24 of an initial Form 22 through Input Devices 10ID and Interface Mechanism 20 will read and parse the data in the Fields 24 of the Form 22, query the associated databases with the data, and read out and display information pertaining to that patient, either in the same Form 22 or in another Form 22. The user may then enter additional data into that or an associated Form 22, such as an identification of the purpose of the current patient encounter, such as a periodic review and assessment of the patient's lipid levels. Interface Mechanism 20 will then call up and display one or more Forms 22 having Fields 24 displaying relevant information, such as data from the patient's medical records or the results of new tests, and so on. The user may then, for example, review the historical data, compare the historical data to new data, or enter new data, and so on. Interface Form Editors 22, such as the Encounter Form Editor® provided in MedicaLogic/Medscape Logician®, are well known in the art and need not be discussed in further detail further herein.

As illustrated in FIG. 2, Medical Processes 10MED of the present invention include one or more Medical Support Processes 10MSP and one or more associated Medical Databases 10MDB wherein Medical Databases 10MDB include Medical Record Databases 28 and may include one or more Medical Support Databases 30. Medical Record Databases 28 may include one or more Medical Records 28R for and corresponding to each patient, depending upon types and sources of information comprising each patient's records. Medical Record Databases 28 are constructed and used in the conventional manner to store, manage and retrieve patient Medical Records 28R and are, for example, generated, stored, managed and retrieved by and through EMR 12, as discussed briefly above. Medical Support Databases 30, in turn, contain medical information used in the medical support functions described below and may be constructed or provided from a variety of sources, but typically may be accessed by EMR 12 or EMR 12 related mechanisms of the MSS 10, such as Interface Mechanism 20. As will be described in the following, Medical Support Databases 30 may be implemented in a variety of forms, such as separate databases for the various types of medical support processes provided or as data integrated into the medical support processes.

Next considering the Medical Support Processes 10MSP provided and executed by a MSS 10 of the present invention, it is recognized that each interaction between a medical practitioner and a patient may be regarded as comprising one or more "encounters". An "encounter" may in turn be defined as a procedure of one or more steps that are primarily focused upon or involved with a given medical issue and the encounters may be of variable scope or complexity. For example, a general primary physical examination comprises one or more encounters of relatively wide scope, encompassing a wide range of medical information, but of relatively low complexity, such as testing or determining whether a variety of basic medical variables are within accepted ranges Other encounters may be of lesser scope but greater depth, such as an encounter focused on control of lipid levels or of an asthma treatment, or may comprise several encounters which may be independent of one another or which may overlap or be related.

Figure 3:
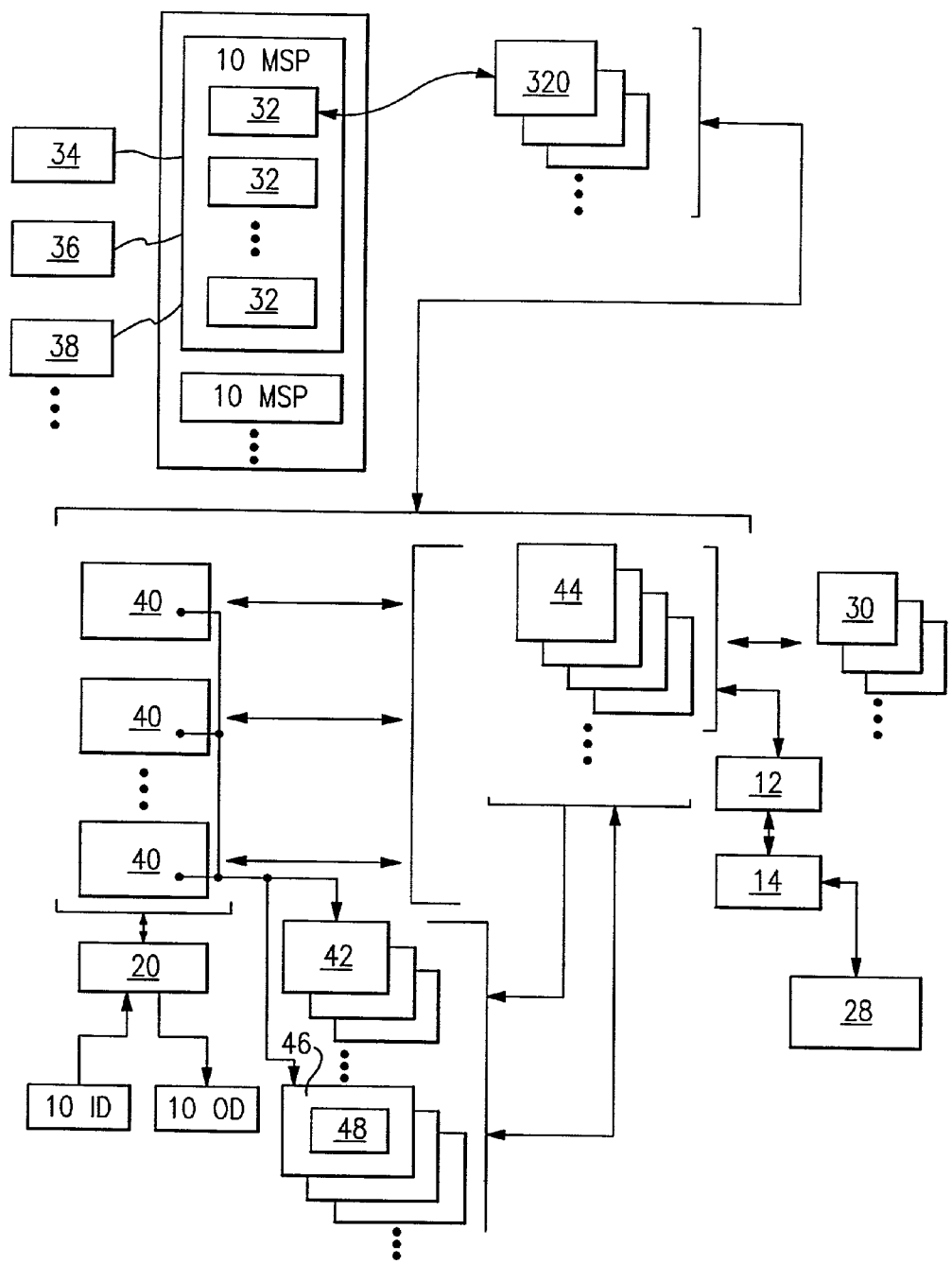
FIG. 3 is a block diagram illustrating medical support processes of the present invention.

Referring to FIG. 3, in a presently preferred embodiment of a MSS 10, Medical Processes 10MED include and support one or more Medical Support Processes 10MSP wherein each Medical Support Process 10MSP corresponds to a specific type of encounter. For example, one Medical Support Process 10MSP may implement a medical process for the control of lipid levels while another may implement procedures for the evaluation, diagnosis and treatment of asthma or a cardiac condition. As illustrated in FIG. 3, a Medical Support Process 10MSP comprises a plurality of Process Phases 32 wherein each Process Phase 32 is focused on a certain aspect or aspects of the Medical Support Process 10MSP and comprises one or more Process Operations 32O. For example, a typical Medical Support Process 10MSP may include two basic Process Phases 32, respectively referred to as the Data Capture (Data) Phase 34 and the Assessment/Diagnosis (Assessment) Phase 36, and may include a third basic Process Phase 32, referred to as the Recommendations Phase 38.

A Data Phase 34 is generally comprised of operations to acquire, enter and review historical and new information pertaining to the medical condition of a patient for the purposes of the current encounter, and may typically be performed by a nurse or para-practitioner. Such operations may include, for example, entry of the current date, entry of current measurements, such as blood pressure and heart rate, the entry or confirmation of entry of current or recent tests or procedures, such as blood or cholesterol screening, the entry of information from the patient, such as recent number and severity of asthma attacks, and so on, and the review of the present and historical information, including medication and other treatment plans. The procedures of Data Phase 34 will often include the generation of prompts and reminders to the user. Such prompts and reminders will typically be dependent upon the purpose of the encounter and, for example, may insure that information necessary to or desirable the procedure are acquired and entered. For example, the user may be prompted to determine and enter a current blood pressure, heart rate and weight, to ask certain relevant questions of the patient, such as the patient's perceptions of the effects of a medication, and so on.

The Assessment Phase 36 would typically be performed by a practitioner or para-practitioner and is essentially comprised of procedures to assess the patient's condition and treatment based upon the information acquired or updated in Data Phase 34 and, for example, to assist in the diagnosis of the patient's condition and treatment. For example, procedures of Assessment Phase 36 may present medical guidelines for assessment and treatment of the severity or level of a patient's condition based upon current information and may suggest tests or procedures to be performed or that should be performed at regular intervals or that are due to be performed Assessment Phase 36 may also include procedures to suggest reminders of other conditions that may arise from or be related to the patient's current condition or that may result in similar symptoms and should be considered, and so on Other information provided to the user may include suggested medications, including the effects, side effects and interaction effects of the medications, reminders of medications that have been used previously or other medications currently being used by the patient for other reasons, and so on. As described herein above, however, all such reminders, suggestions and prompts are presented to the practitioner as reminders and suggestions and the user may override such reminders, suggestions and prompts based, for example, the practitioner's experience or knowledge of the particular patient or of other factors, and will typically be provided with fields to enter the reasons for disagreement with the guidelines, which will be automatically entered in the patient's Medical Records 28R as a reminder to the practitioner at the next encounter with the patient.

A Medical Support Process 10MSP may also include a Recommendations Phase 38, which is typically primarily comprised of procedures to assist the practitioner in determining a course of treatment for the patient, based upon currently accepted guidelines and standards of practice in the field and for the condition of interest. These procedures may provide guidelines regarding possible medications and recommended medication levels, including the effects, side effects and interaction effects of the medications, reminders of medications that have been used previously or other medications currently being used by the patient for other reasons, suggestions for forms of treatment, suggestions for further tests and similar procedures, and so on. Although many of the Recommendations Phase 38 procedures may overlap procedures that may appear in the associated Assessment Phase 36, the procedures of the Recommendations Phase 38 will typically be in greater depth and at a greater level of detail than will those of the Assessment Phase 36.

It must be noted that a Recommendations Phase 38 may not be necessary for a given Medical Support Process 10MSP, or could be an extensive supplement to the Medical Support Process 10MSP, depending on the problem, condition or disease addressed by the Medical Support Process 10MSP. It must also be noted that the Process Operations 32O of a Recommendations Phase 38 will operate to thoroughly integrate the decision and recommendation support prompts and suggestions provided by the Recommendations Phase 38 with the patient specific information, including both the historical information acquired from Medical Records 28R and the current information acquired in the Data Phase 34, so that all recommendations, suggestions and prompts are specific to and tailored to that patient at that time. For example, the patient specific information evaluated includes but is not limited to patient demographics, such as age, sex, height, weight, and so on, problems particular and specific to the patient, current and previous medications, allergies, lab values, that is, the results of laboratory tests and procedures, and patient specific observations, such as whether lipid goals have been met, and so on.

It will be apparent that the number, arrangement and relationships between Process Phases 32 in a Medical Support Process 10MSP will depend upon the nature, scope and complexity of the Medical Support Process 10MSP and of the encounter. For example, in certain Medical Support Processes 10MSP the Data Phase 34 and the Assessment Phase 36 or the Assessment Phase 36 and the Recommendations Phase 38 may be integrated or combined into a single Process State 32, or certain Process Phases 32, such as a Recommendations Phase 38, may not be required in a given Medical Support Process 10MSP. It will also be apparent that a given Medical Support Process 10MSP may include additional Process Phases 32 for specific purposes, or that a given Process Phase 32 may be organized as a number of Process sub-Phases 32 for convenience, ease of use or clarity. It will also be recognized that the number, design, arrangement and relationship among the Process Forms 40 of each Process Phase 32 will be dependent upon similar factors and judgments, as well as such factors as the graphics display capabilities of the Output Devices 10OD of the MSS 10 in which the Medical Support Processes 10MSP are implemented. For example, a laptop to a desktop computer with relative high graphic display capabilities may arrange and display more information in each Process Form 40, while the more limited capabilities of, for example, a palmtop device or even a cell phone type device may require that the Process Phases 32 be implemented through a greater number of simpler Process Forms 40.

In a typical implementation of a Medical Support Process 10MSP, the Process Phases 32 and Process Operations 32O of the Medical Support Processes 10MSP are implemented and executed through Process Forms 40 and associated Support Processes 44, together with the Medical Records 28R and Medical Support Databases 30 associated with the Process Operations 32O.

Process Forms 40 and Interface Mechanism 20 comprise the interface and mechanism through which a user interacts with the Process Operations 32O comprising each Process Phase 32 of a Medical Support Process 10MSP. As described, each Process Form 40 comprises a structured array of Fields 42 for the display and entry of data, text, graphics, prompts, messages, commands, "pop-up windows", and so on. For example, a Medical Support Process 10MSP may be initially represented by an initial Process Form 40 which presents an index of the Process Phases 32 comprising the Medical Support Process 10MSP, and "clicking" on an index tab or field may call up the first of one or more Process Forms 40 comprising the selected Process Phase 32. Within a Process Form 40 of a Process Phase 32, and as discussed further below, the user will be presented with Fields 42 for interacting with one or more Process Operations 32O comprising the Process Phase 32, such as Fields 42 for entering and displaying information or prompts pertaining to one or more Process Operations 32O. Process Forms 40 may be created, for example, by the Interface Form Editor 22 of the Interface Mechanism 20 of the EMR 12, although a Process Form Editor 40E similar to an Interface Form Editor 22 may be created specifically for this purpose.

Next considering Support Processes 44, the Process Operations 32O of each Process Phase 32, are implemented by and in Support Processes 44, each of which is an interactive process or program for performing a Process Operation 32O. In this regard, and as indicated in FIG. 3, certain Fields 42 of Process Forms 40, indicated as Process Fields 46, contain Process Calls 48 wherein each Process Call 48 is a reference, designator, "call" or invocation to or of a corresponding Support Process 44. That is, and for example, an action with respect to a Process Field 46, such as the entry of data or of a decision or command, including "clicking" on the Process Field 46 to invoke a corresponding action or activity, will in turn invoke or call a corresponding Support Process 44. In another instance, a Support Process 44 may invoke another Support Process 44, the selection of may be dependent upon the nature and results of the calling Support Process 44. In another example, multiple Process Fields 46 may refer to the same Support Process 44, as when two or more Process Fields 46 of a Process Form 40 invoke a Support Process 44 that invokes the next Process Form 40 in a sequence or group of Process Forms 40. In other instances, and again for example, the value or decision entered into a Process Field 46 may determine the Support Process 44 that is called, as when the entry of a value or decision in a Process Field 46 calls a Support Process 44 that checks the value or decision entered in a Process Field 46 and the result of the check determines the path of execution through the Support Process 44, or another Support Process 44 to be invoked. In other examples, Support Processes 44 may confirm that all necessary data is present in the Fields 42 of a Process Form 40, whether the time elapsed since a periodic test or procedure was last performed has exceeded recommended limits, or whether the test or procedure was performed at all. Other Support Processes 44 may compare the values contained in Fields 42, such as current diagnostic or test conditions and medication types of levels, and may display a prompt or suggestion or diagnosis when the values indicate a potential problem or suggest a medication or change in medication, and so on. Those of ordinary skill in the relevant arts will thereby appreciate that Support Processes 44 and Process Forms 40 allow the construction of Process Operations 32O and Medical Support Process 10MSP of any desired extent or complexity.

Finally, Medical Records 28R and the Medical Support Databases 30, the Medical Records 28R involved in the performance of a Medical Support Process 10MSP will be comprised of the Medical Records 28R of the patient that is the subject of the encounter and will typically include the patient's historical Medical Records 28R, together with new data pertaining to the patient, such as reports containing the results of current or recent tests or procedures. As described herein above, the patient Medical Records 28R will typically be accessed through Interface Mechanism 20 of the EMR 12 to read data from the Medical Records 28R or to enter data into the Medical Records 28R, either as a result of user inputs through Input Devices 10ID or by operation of one or more of Support Processes 44.

Medical Support Databases 30, in turn, contain medical information used in the execution of Support Processes 44. Medical Support Databases 30 will contain, for example, ranges or values of biological measurements, such as blood pressure, lipid levels or frequency and severity of asthma attacks that represent, according to current medical guidelines, either acceptable ranges or ranges indicating a diagnosis of a condition to be treated, guidelines for medications and medication levels, guidelines for tests or other procedures, including guidelines as to the frequency of tests and procedures, and so on. As described herein above, Medical Support Databases 30 may be constructed or provided from a variety of sources, and may be accessed, for example, through the Interface Mechanism 20 of the EMR 12 or equivalent mechanisms. Medical Support Databases 30 will typically be accessed by operation of and through Support Processes 44, although user inputs through Input Devices 10ID may be used to directly access Medical Support Databases 30 in certain circumstances.

It will be appreciated and understood by those of ordinary skill in the relevant arts that Process Forms 40 and Medical Records 28R may be constructed, maintained and accessed by means of, for example, an Interface Form Editor 22 of an Interface Mechanism 20 of an EMR 12, or by similar mechanisms. It will also be appreciated and understood by those of ordinary skill in the relevant arts that Support Processes 44 and Medical Support Databases 30 may be implemented in a variety of forms and by use of a variety of utilities or tools, including an Interface Form Editor 22 of an EMR 12 as the Interface Mechanisms 20 of many EMR 12s support at least some degree of programming capability.

In this regard, Support Processes 44 and Medical Support Databases 30 may be constructed as separate entities, that is, as a library of processes, programs or routines for performing Process Operations 32O and as one or more databases containing information extracted from current medical practice guidelines or recommendations that is accessed as required by the Support Processes 44. As discussed, the information included in Medical Support Databases 30 may include, for example, ranges or values of biological measurements, such as blood pressure, lipid levels or frequency and severity of asthma attacks that represent, according to current medical guidelines, either acceptable ranges or ranges indicating a diagnosis of a condition to be treated, guidelines for medications and medication levels, guidelines for tests or other procedures, including guidelines as to the frequency of tests and procedures, and so on. This method for implementing Support Processes 44 and Medical Support Databases 30 is generally advantageous in allowing Support Processes 44 and Medical Support Databases 30 to be readily and independently modified, updated or extended as needed. A disadvantage of this method, however, is that the construction of Support Processes 44 and Medical Support Databases 30 is by processes more familiar to a programmer than to a medical practitioner, and that is thereby distanced from the methods and patterns of thought and practice of the medical practitioner, who is the primary user of the system and the primary source of information regarding the procedures that are to be implemented in Medical Support Processes 10MSP.

For the above reasons, Support Processes 44 and Medical Support Databases 30 are implemented in a presently preferred embodiment of MSS 10 in a form and by a procedure that more closely reflects the methods and patterns of thought and practice of the medical practitioner. For this reason, Support Processes 44, Process Forms 40 and Medical Support Processes 10MSP may be readily constructed by persons whose primary training and experience are in the medical rather than in programming, while is advantageous in that the Medical Support Processes 10MSP more closely reflect actual medical practice. More specifically, Support Processes 44 are presently implemented as sequences of "if-then-else" programs or procedures while and the data of Medical Support Databases 30 is integrated directly into the "if-then-else" statements, or into Fields 42 or "windows" of Process Forms 40.

Lastly, it will be noted that it is common for medical practitioners to use variant forms or terms in referring to, for example, a procedure, measurement, test, medication or condition. The specific form or term used by a practitioner may depend, for example, upon the age and experience of the practitioner, when and where the practitioner attended medical school or subsequently practiced, and so on. For this reason, a MSS 10 of the present invention may further include a Dialect Translator 50 operating in conjunction with Interface Mechanism 20 to translate between terms and forms used by a given practitioner and a common, standard or standardized set of terms and forms. Dialect Translator 50 includes a Dialect Text File 50D for each practitioner using a given MSS 10 wherein the Dialect Text File 50D contains standardized terms and forms as used in Process Forms 40 and wherein the Dialect Text File 50D is indexed by terms and forms specified by or for a given practitioner. Dialect Translator receives terms and forms entered by that practitioner through Input Devices 10ID, and provides the corresponding standard term or form. Dialect Translator 50 also operates in the reverse by reading standard terms and forms appearing in Process Forms 40 and translating the standard terms and forms into the dialect terms and forms preferred by the practitioner in the Process Forms 40 as displayed to the practitioner through Display 10DS.

Figure 4H:
Figure 4J:
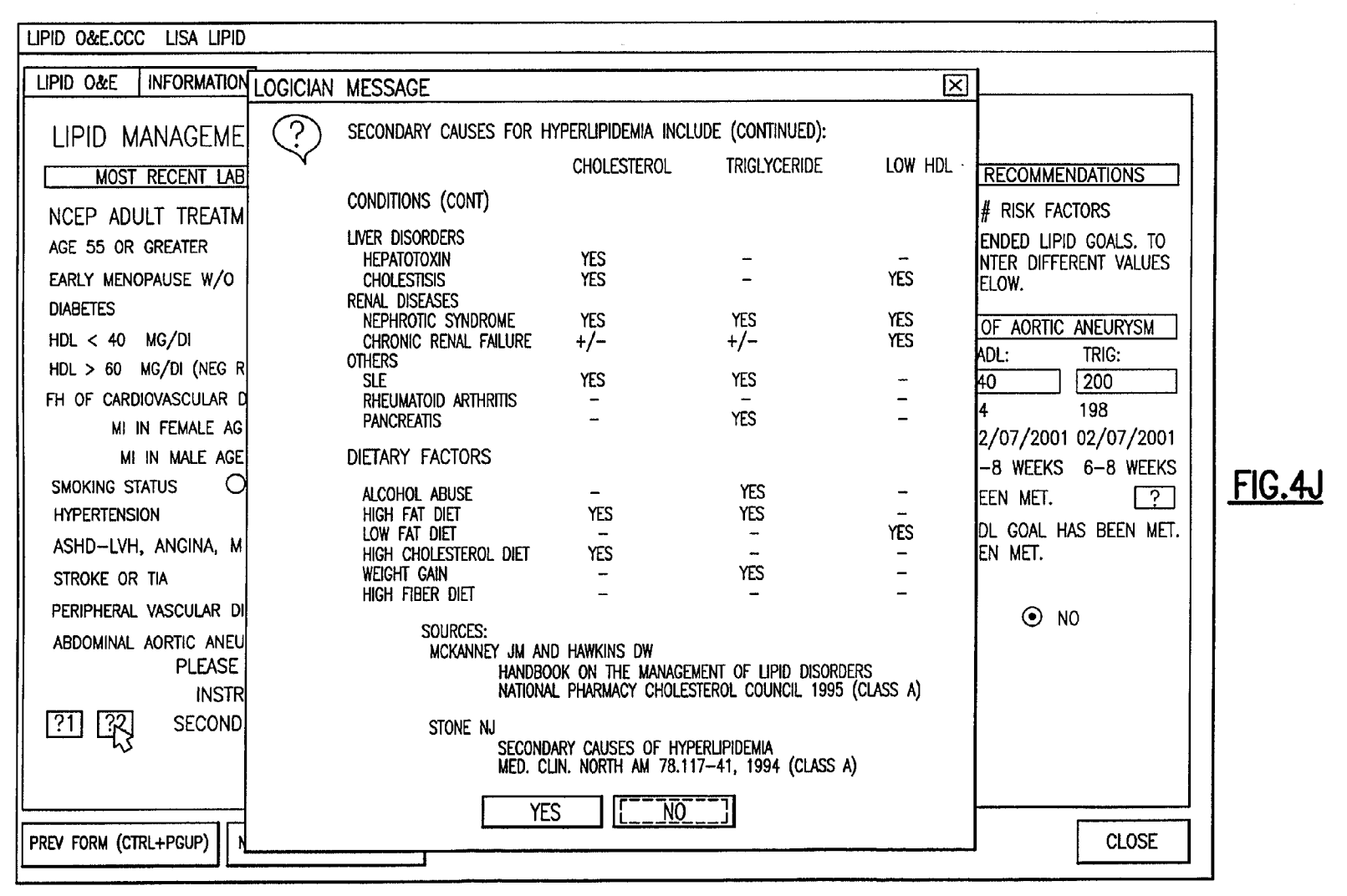
Figure 4L:

Lastly, in this regard, FIGS. 4A through 4B comprise illustrations of Process Forms 40, the Fields 42 and Process Fields 46 of the Process Forms 40, and Support Processes 44 of an exemplary Medical Support Process 10MSP and, in particular, a Medical Support Process 10MSP for the monitoring and control of lipids, which is a generally recognized significant medical problem. In FIGS. 4A through 4M, FIGS. 4A through 4K illustrate the Process Forms 40 of a Process Phase 32 in which the Data Phase 34 and Diagnostic Phase 36 of the Medical Support Process 10MSP are interleaved, but which begins with Process Forms 40 primarily directed to Data Phase 34 processes and shifts toward Diagnostic Phase 36 processes. For example, and it will be noted that each of these Process Forms 40 contains fields for displaying and entering information relating to the patient, such as age, related conditions or diseases, current cholesterol, LDL, HDL and triglyceride levels, and goal cholesterol, LDL, HDL and triglyceride levels, either as yes/no decisions/data or as numeric data, and so on. In FIG. 4A, for example, the user is prompted to enter a diagnosis of hyperlipidemia to the patient problem list, if appropriate. In FIG. 4B the user requests the current professional guidelines for cholesterol, LDL, HDL and triglyceride levels if the patient is diabetic, and in FIG. 4C repeats the process of Step 4B for additional risk factors. In FIG. 4D the user requests that the patients most recent lab measurements be displayed, for example, for comparison with the guideline cholesterol, LDL, HDL and triglyceride levels, and in FIG. 4E the user requests the cholesterol, LDL, HDL and triglyceride level guidelines for the patient's current risk factors. In FIGS. 4F and 4G, the user requests information pertaining to the diagnosis steps performed in FIGS. 4A through 4E by requesting information regarding the categories of risks that were used in determining the patient risk profile. FIGS. 4F and 4G respectively illustrate the system responses for CV risk factors of 6% and 21%, and in FIG. 4H the Medical Support Process 10MSP provides the user with a message further explaining the risk factors. In FIGS. 4I and 4J the user and support process have reverted to the Process Form 40 illustrated in FIG. 4A, but which is now modified to provide user prompts/reminders as to whether the user has considered other causes of hyperlipidemia and, upon query by the user, displays two message pages of information relating to secondary causes of hyperlipidemia, wherein the user can enter information regarding those factors considered by the user. FIG. 4K continues this process by providing criteria for recommended periods or intervals for repeated lipid profiles for various conditions. In FIGS. 4L and 4M, the Medical Support Process 10MSP enters a Recommendations Phase 38 wherein the Medical Support Process 10MSP provides messages containing therapy or treatment/medication recommendations based on current professional guidelines and the patient information and diagnosis that were entered or reached in the Data Phase 34 and Diagnosis Phase 36 illustrated in FIGS. 4A through 4J.

Lastly, in this regard, Appendix A to the Specification contains a listing of the "if-then-else" statements comprising the Support Processes 44 for the Medical Support Process 10MSP, illustrated in FIGS. 4, as an exemplary implementation of a Medical Support Process 10MSP.

In summary, therefore, and as illustrated and described herein above, a system and method of the present invention include or employ medical records relating to the patients and medical support databases including medical guidelines for the diagnosis and treatment of medical conditions according to current professional guidelines for the diagnosis and treatment of diseases and medical conditions and processes utilizing these databases to diagnose and recommend therapy or treatment for a patient in a manner that is supportive of but that does not interfere with the work and mind flow processes of the user. As described, a support process performed by a medical support system of the present invention executes an interactive dialogue between the medical support process and the user to provide guidance to the user in performing the medical support process according to the guidelines and dependent upon the user inputs and the medical record. A medical support process performed by the present invention for a given condition or disease includes one or more process phases, which may include a data entry and review phase, a diagnostic phase and a therapeutic/treatment recommendations phase, which are presented to a user through process forms providing graphic interfaces for the entry and display of information regarding the support process.

Figure 5:
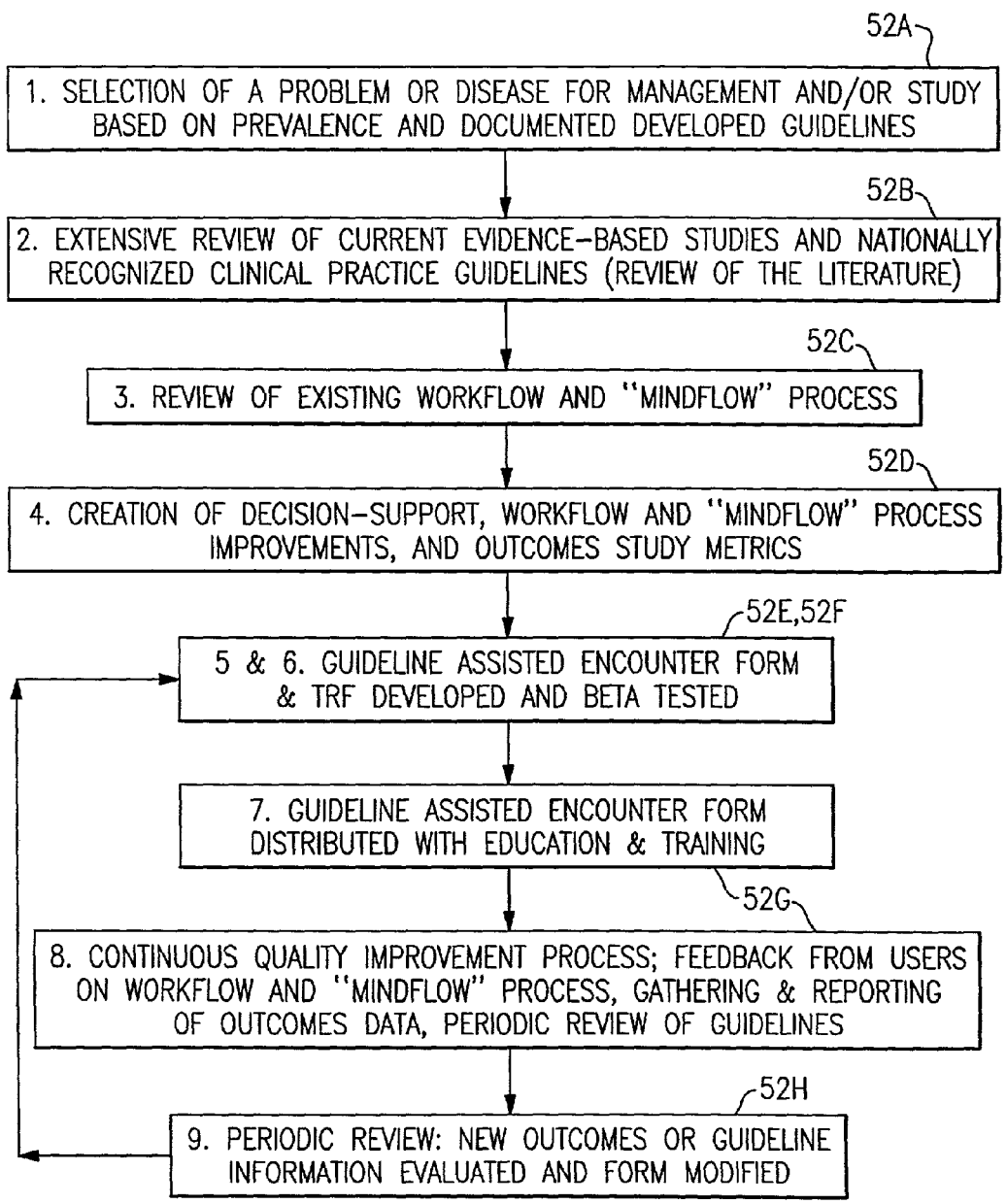
FIG. 5 is a flow diagram illustrating the generation and maintenance of a medical support process.

Finally, the procedure for constructing a Medical Support Process 10MSP is illustrated in FIG. 5 and includes the steps of:

Step 52A: Selection of a problem or disease for management and/or study.

The process of designing a guideline-assisted Medical Support Process 10MSP requires selecting a problem or disease to be the subject of the Medical Support Process 10MSP. This step may be based upon evidence-based nationally recognized and published clinical practice guidelines or upon a selected local, regional, or private criteria.

Step 52B: Review of current evidence-based studies and nationally recognized clinical practice guidelines, including review of the literature.

An extensive review of the literature provides the foundation for developing consensus current professionally accepted guidelines pertinent to the subject of the Medical Support Process 10MSP and creating of the guideline-assisted Medical Support Process 10MSP. For example, the Agency for Healthcare Quality Research (AHQR) is presently the overseer of the National Guidelines Clearing House and, for example, can serve as a starting point. Peer review journals with evidence-based outcome studies may also be sources of guideline criteria.

Step 52C: Review of existing workflow and "mind flow" process.

The day-to-day, step-by-step workflow required in the evaluation and treatment of the chosen problem or disease is mapped out for the average provider and practice and the thought process of the provider and patient are studied to map out the most time efficient entry and display of information, guideline prompts, and clinical decision support.

Step 52D: Creation of decision-support, workflow and "mind flow" process improvements, and outcome study metrics.

Based on the evaluation of information gathered in Step 50C on the problem or disease and existing work flows, improved work flow and "mind flow" processes are developed to be implemented in the Medical Support Process 10MSP, as are the quality and outcome study metrics to be incorporated into the Medical Support Process 10MSP.

Step 52E: Development of a guideline-assisted Medical Support Process 10MSP.

Step 52E-1: A "shell" Medical Support Process 10MSP is developed which includes all Process Operations 32O and Process Forms 40, the quality and outcome study metrics, and the enhanced workflow and "mind flow" processes.

Step 52E-2: A range and variety of decision support prompts are reviewed to provide the most efficient and timely but least intrusive assistance, including, for example, data displays, visibility regions and modal dialogue boxes, and the most effective are incorporated into the Medical Support Process 10MSP.

Step 52E-3 The work flow and "mind flow" of the Medical Support Process 10MSP are reevaluated and the Medical Support Process 10MSP is preferable then tested in real clinical practices with real patients and any corrections or modification indicated as a result of the tests are incorporated into the Medical Support Process 10MSP.

Step 52F: Development of a Recommendations Phase 38.

As described and depending on the problem, condition or disease addressed by the Medical Support Process 10MSP, a Recommendations Phase 38 may not be necessary or could be an extensive supplement to the Medical Support Process 10MSP. As described, in those instances where a Recommendations Phase 38 is required, Steps 52E will include the additional Step 52F of constructing a Recommendations Phase 38 which, as described, is constructed as Process Operations 32O based on series or strings of "if-then-else" statements that evaluate past and current patient specific information from the databases, patient demographics, such as age, sex, height, weight, and so on, problems particular and specific to the patient, current and previous medications, allergies, lab values, that is, the results of laboratory tests and procedures, and patient specific observations, such as whether lipid goals have been met, and so on.

Step 52G: User Review.

Each Medical Support Process 10MSP is continuously reviewed on the basis of information from users of the Medical Support Process 10MSP, and is modified as indicated by information from the users.

Step 52H: Guideline Review.

The guidelines and current recommended medical practices incorporated into each Medical Support Process 10MSP are continuously reviewed from all available sources and changes in the accepted and recommended guidelines and practices are incorporated into each Medical Support Process 10MSP as the recommended guidelines and practices are updated.

In conclusion, while the invention has been particularly shown and described with reference to preferred embodiments of the apparatus and methods thereof, it will be also understood by those of ordinary skill in the art that various changes, variations and modifications in form, details and implementation may be made therein without departing from the spirit and scope of the invention as defined by the appended claims. For example, Processes 32O and Medical Support Databases 30 may be implemented in a wide variety of ways and forms, and the fundamental decision/process support mechanisms and methods of the present invention may be applied to and implemented for a wide range of complex analysis/decision/procedural situations. Therefore, it is the object of the appended claims to cover all such variation and modifications of the invention as come within the true spirit and scope of the invention.

What is claimed is:

1. a medical support system including a memory for storing at least one medical support process relating to diagnosis and treatment of a medical condition, a processor responsive to the medical support process and to user inputs for performing the medical support process, an input device for user inputs relating to the medical support process and an output device for displaying the results of the medical support process to a user, comprising:
    at least one medical record relating to a patient;
    at least one medical support database including medical guidelines for the diagnosis and treatment of the medical condition;
    a bi-directional dialect translator for receiving and translating between preferred dialect medical terms entered by an individual user and corresponding equivalent but different standard medical terms employed in the support operations, conversely bi-directionally translating the standard medical terms employed by the support operations into the preferred dialect medical terms originally entered and used by the individual user for display to the user; and
    a medical support process including at least one process phase each process phase including one or more process operations;
    each of the process operations of a process phase including:
        at least one process form providing an interface between a user and the process operations of the process phase, each process form including fields for passing user inputs to the process operations and for displaying the results of the process operations to the user; and
        at least one support process responsive to user inputs, the medical record and the guidelines for performing the process operations, wherein:
        the support processes execute an interactive dialogue between the medical support process and the user to provide guidance to the user in performing the medical support process according to the guidelines and dependent upon the user inputs and the medical record,
        wherein the guidance provided to the user is capable of being overridden by the user and wherein the overridden guidelines are dynamically updated with a patient based guideline for the individual patient based on user input and the medical record for the individual patient.

2. The medical support system of claim 1, wherein a medical support process includes:
    a data phase for entering new information and reviewing historical information pertaining to the medical condition of the patient for the purposes of the medical support process; and
    an assessment phase for evaluation of the patient's present medical condition based upon the information from the data phase and the guidelines for the diagnosis and treatment of the medical condition.

3. The medical support system of claim 2, wherein a medical support process further includes:
    a recommendations phase including process operations and guidelines to assist the user in determining a course of treatment for the patient.

4. The medical support system of claim 1, wherein the process form fields include fields for the display and entry of data, text, prompts, messages and user decision options.

5. The medical support system of claim 1, wherein the process form fields include process fields containing process calls invoking corresponding support processes upon corresponding user inputs to the process fields.

6. The medical support system of claim 1, wherein the support operations include first support processes for invoking second support processes dependent upon user inputs.

7. The medical support system of claim 1, wherein the support processes include support processes for displaying a next process form.

8. The medical support system of claim 1, wherein the support processes include support processes for modifying the information displayed in a present process form.

9. The medical support system of claim 1, wherein the medical support databases reside within the support processes.

10. The medical support system of claim 1, wherein user input used to override the guidance is entered in the medical record.

11. a medical support system including an input device for user inputs relating to a medical process and an output device for displaying the results of the medical process to a user, a memory for storing the medical process and medical data, and a processor operating under control of the medical process and the user inputs, a method for providing support for a medical practitioner performing medical process relating to diagnosis and treatment of a medical condition, comprising the steps of:

storing at least one medical record relating to a patient;

storing at least one medical support database including medical guidelines for the diagnosis and treatment of the medical condition;

translating bi-directionally between preferred dialect medical terms used and entered by a user and corresponding equivalent but different standard medical terms employed in the support operations and, conversely translating bi-directionally the standard medical terms employed by the support operations into the preferred dialect medical terms originally entered and used by the individual user for display to the user; and performing a medical support process including at least one process phase each process phase; each process including one or more process operations;

each of the process operations of a process phase including;

providing at least one process form providing an interface between a user and the process operations of the process phase, each process form including fields for passing user inputs to the process operations and for displaying the results of the process operations to the user; and providing at least one support process responsive to user inputs, the medical record and the guidelines for performing the process operations, wherein the support processes execute an interactive dialogue between the medical support process and the user to provide guidance to the user in performing the medical support process according to the guidelines and dependent upon the user inputs and the medical record, wherein the guidance provided to the user is capable of being overridden by the user and wherein the overridden guidelines are dynamically updated with a patient based guideline for the individual patient based on user input and the medical record for the individual patient.

12. The method of claim 11 for providing support for a medical practitioner performing the medical process, wherein a medical support process includes:

a data phase for entering new information and reviewing historical information pertaining to the medical condition of the patient for the purposes of the medical support process; and an assessment phase for evaluation of the patient present medical condition based upon the information from the data phase and the guidelines for the diagnosis and treatment of the medical condition.

13. The method of claim 12 for providing support for a medical practitioner performing the medical process, wherein a medical support process further includes:

a recommendations phase including process operations and guidelines to assist the user in determining a course of treatment for the patient.

14. The method of claim 11 for providing support for a medical practitioner performing the medical process, wherein the process form fields include fields for the display and entry of data, text, prompts, messages and user decision options.

15. The method of claim 11 for providing support for a medical practitioner performing the medical process, wherein the process form fields include process fields containing process calls invoking corresponding support processes upon corresponding user inputs to the process fields.

16. The method of claim 11 for providing support for a medical practitioner performing the medical process, wherein the support operations include first support processes for invoking second support processes dependent upon user inputs.

17. The method of claim 11 for providing support for a medical practitioner performing the medical process, wherein the support processes include support processes for displaying a next process form.

18. The method of claim 11 for providing support for a medical practitioner performing the medical process, wherein the support processes include support processes for modifying the information displayed in a present process form.

19. The method of claim 11 for providing support for a medical practitioner performing the medical process, wherein the medical support databases reside within the support processes.

20. The method of claim 11, wherein user input used to override the guidance is entered in the medical record.

\* \* \* \* \*

UNITED STATES PATENT AND TRADEMARK OFFICE
CERTIFICATE OF CORRECTION

PATENT NO. : 7,577,573 B2  Page 1 of 1
APPLICATION NO. : 10/017652
DATED : August 18, 2009
INVENTOR(S) : Janas, III et al.

It is certified that error appears in the above-identified patent and that said Letters Patent is hereby corrected as shown below:

Column 15, line 44 (Claim 1) should read:   --A medical support system including a memory for storing--.

Column 16, line 62 (Claim 11) should read:   --A medical support system including an input device for--.

Column 17, line 30 (Claim 11) should read:   --forming the process operations, wherein:--.

Signed and Sealed this

Twenty-seventh Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,577,573 B2  Page 1 of 1
APPLICATION NO. : 10/017652
DATED : August 18, 2009
INVENTOR(S) : Janas, III et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1641 days.

Signed and Sealed this

Seventh Day of September, 2010

David J. Kappos
*Director of the United States Patent and Trademark Office*